(12) United States Patent
Gigante

(10) Patent No.: US 11,122,164 B2
(45) Date of Patent: Sep. 14, 2021

(54) METHOD FOR PROVIDING REMOTE ASSISTANCE SERVICES USING MIXED AND/OR AUGMENTED REALITY VISORS AND SYSTEM FOR IMPLEMENTING IT

(71) Applicant: PREDICT SRL, Bari (IT)

(72) Inventor: Angelo Aurelio Gigante, Molfetta (IT)

(73) Assignee: PREDICT SRL, Bari (IT)

( * ) Notice: Subject to any disclaimer, the term of this patent is extended or adjusted under 35 U.S.C. 154(b) by 0 days.

(21) Appl. No.: 16/635,455

(22) PCT Filed: Aug. 1, 2018

(86) PCT No.: PCT/IB2018/055777
§ 371 (c)(1),
(2) Date: Jan. 30, 2020

(87) PCT Pub. No.: WO2019/025997
PCT Pub. Date: Feb. 7, 2019

(65) Prior Publication Data
US 2021/0136226 A1    May 6, 2021

(30) Foreign Application Priority Data
Aug. 1, 2017  (EP) .................................. 17425085

(51) Int. Cl.
*H04M 3/51*     (2006.01)
*G16H 40/67*    (2018.01)
(Continued)

(52) U.S. Cl.
CPC .......... *H04M 3/5191* (2013.01); *G06Q 10/20* (2013.01); *G06T 19/006* (2013.01); *G16H 40/67* (2018.01); *H04N 7/142* (2013.01)

(58) Field of Classification Search
CPC ...... G06Q 10/20; G06T 19/006; G16H 40/67; H04M 3/5191; H04N 7/142
(Continued)

(56) References Cited

U.S. PATENT DOCUMENTS 9,088,787 B1    7/2015  Smith et al.
9,843,678 B2 *  12/2017 Maxwell .............. H04M 11/045
(Continued)

FOREIGN PATENT DOCUMENTS

WO    2017/072616 A1    5/2017

OTHER PUBLICATIONS

International Search Report, dated Sep. 20, 2018, from corresponding PCT application No. PCT/IB2018/055777.
(Continued)

*Primary Examiner* — Hemant S Patel
(74) *Attorney, Agent, or Firm* — Nixon & Vanderhye

(57) ABSTRACT

A system for providing remote assistance services using mixed and/or augmented reality visors includes the following apparatuses in combination: one or more smartphones/tablets of each user who requests assistance, connectable to any mixed/augmented reality visor on which a specific app is installed; one or more operator stations with PC/tablet configured to be able to communicate in real time with the devices of the user requesting assistance; at least one server configured to manage a database and to be connectable to and interfaceable with the smartphones/tablets of the users and the PCs/tablets of the operators; wherein the smartphones, tablets, PCs, visors and servers are connected to implement the following software components, which are all connectable to an Internet network: ADMINISTRATOR WEB FRONTEND, BACKEND, REAL TIME DATABASE, OPERATOR DESKTOP APP, RELATIONAL
(Continued)

DATABASE, CLIENT MOBILE APP, OPTIP MIXED/
AUGMENTED REALITY VISOR APP, EMAIL SERVICE.

3 Claims, 16 Drawing Sheets

(51) Int. Cl.
*G06Q 10/00* (2012.01)
*G06T 19/00* (2011.01)
*H04N 7/14* (2006.01)

(58) Field of Classification Search
USPC ........... 348/14.01–14.16; 379/265.01–266.1;
709/201–207, 217–248
See application file for complete search history.

(56) References Cited

U.S. PATENT DOCUMENTS

| | | | | | |
|---|---|---|---|---|---|
| 2002/0168054 | A1* | 11/2002 | Klos | ........................ | H04M 3/22 |
| | | | | | 379/1.04 |
| 2004/0075738 | A1* | 4/2004 | Burke | .............. | G08B 13/19656 |
| | | | | | 348/143 |
| 2005/0213743 | A1* | 9/2005 | Huet | ...................... | G06Q 10/10 |
| | | | | | 379/265.09 |
| 2006/0052169 | A1* | 3/2006 | Britt | .................... | G07F 17/3234 |
| | | | | | 463/42 |
| 2008/0118052 | A1* | 5/2008 | Houmaidi | ........... | H04M 3/5232 |
| | | | | | 379/265.11 |
| 2014/0278730 | A1* | 9/2014 | Muhart | .............. | G06Q 10/0635 |
| | | | | | 705/7.28 |
| 2016/0246943 | A1* | 8/2016 | Lake | ...................... | G16H 10/60 |
| 2016/0253563 | A1* | 9/2016 | Lam | .................... | G06F 11/0748 |
| | | | | | 348/130 |

OTHER PUBLICATIONS

Written Opinion, dated Sep. 20, 2018, from corresponding PCT application No. PCT/IB2018/055777.
Written Opinion, dated Jun. 27, 2019, from corresponding PCT application No. PCT/IB2018/055777.
Notification of Transmittal of the International Preliminary Report on Patentability, dated Sep. 16, 2019, from corresponding PCT application No. PCT/IB2018/055777.

* cited by examiner

OPTIP powered by Predict

Pending request

| Key | Status | Request | Client | City | Illness | User |
|---|---|---|---|---|---|---|
| yhT46r98-Ys | Pending | 05/30/2021 | Mr. Rossi | Rome | Heart Failure | Remote Operator |

••• OPTIP - Remote Assistance
OPTIP Operator

Client: Mr. Rossi
User: remote operator
Illness: heart failure
Request: 05/30/2021
In charge: 05/30/2021
Status: ON HOLD

[TAKE CHARGE]

[CLOSE REQUEST]

[OPEN]

FIG. 3

OPTIP powered by Predict

Pending request

| Key | Status | Request | Client | City | Device | User |
|---|---|---|---|---|---|---|
| yhT46r98-Ys | Pending | 05/30/2021 | Hospital | Rome | LOGIC S7 | Remote technician |

••• OPTIP - Remote Assistance
OPTIP Operator

Client: Hospital
User: Remote technical support
Device: LOGIC S7
Request: 05/30/2021
In charge: 05/30/2021
Status: ON HOLD

● REQUEST HOLOLENS

C — Hi, I'm the Optip operator. How can I help you?
C — Good morning.
C — I have a problem with the ultrasound scanner.
C — This system startup error appears: "Over temperature error".
C — Please, wear the glasses for the video call.

CLOSE REQUEST

OPEN

FIG. 4

OPTIP powered by Predict

Pending request

| Key | Status | Request | Client | City | Device | User |
|---|---|---|---|---|---|---|
| yhT46r98-Ys | Pending | 05/30/2021 | Hospital | Rome | LOGIC S7 | Remote technician |

••• OPTIP - Remote Assistance
OPTIP Operator

Client: Hospital
User: Remote technical support
Device: LOGIC S7
Request: 05/30/2021
In charge: 05/30/2021
Status: ON HOLD

[ TAKE CHARGE ]

[ CLOSE REQUEST ]

[ OPEN ]

FIG. 9

METHOD FOR PROVIDING REMOTE ASSISTANCE SERVICES USING MIXED AND/OR AUGMENTED REALITY VISORS AND SYSTEM FOR IMPLEMENTING IT

BACKGROUND OF THE INVENTION

Field of the Invention

The present invention relates to the field of remote assistance, and in particular to a method for providing a remote presence service, as well as a holopresence call system for implementing it.

According to the invention, the service can be implemented by any mixed/augmented reality visor of known type (e.g. Microsoft Hololens, META, etc.) worn by the person who starts the call.

Description of the Related Art

It is known, from WO 2017/072616 a system for providing remote assistance services using mixed and/or augmented reality visors. A first drawback of such known system is that it is neither disclosed nor suggested the preliminary use of a chat that allows the user to describe the problem to the remote operator, in order to attempt to solve it in real time, without the needing for the user to wear the mixed/augmented reality visor viewer for obtaining remote assistance by chat. A second disadvantage of said known system, is that it is neither disclosed nor suggested the provision of univocal identification elements (such as a QR code) from which the operator giving remote assistance can gain useful information about the calling user, such as anomalies previously found, serial number, type of equipment, identification code of a department, pathologies, etc.

BRIEF SUMMARY OF THE INVENTION

As shown in greater detail below, the present invention provides for a remote operator, by seeing what the user sees in his or her field of vision, being able to interact with the user's ordinary operations by means of real time communications.

The system allows to connect operators, by connecting and assigning the call according to criteria established by rules which can be configured by the assistance provider (e.g. appropriateness, equity, role, retrievability etc.).

According to a particular feature of the invention, there is provided the use of an audio-video connection in holopresence with mixed/augmented reality visors and the transmission of holograms, with HoloBeam Tech or other.

A better understanding of the invention will be achieved by means of the following detailed description and with reference to the accompanying drawings, which relate to two different application scenarios by way of non-limiting example, and more precisely:
for remote assistance on apparatuses;
for medical support on a patient.

BRIEF DESCRIPTION OF THE DRAWINGS

In the drawings:
FIGS. 3 and 4 show some screenshots of the desktop app which can be installed on the called party's PC/tablet;
FIGS. from 5 to 8 diagrammatically show a caller while using the mixed/augmented reality visor, and what he/she sees;
FIG. 9 is a screenshot of the desktop app which can be installed on the called party's PC/tablet, while he/she takes charge of an assistance request.

DETAILED DESCRIPTION OF THE PREFERRED EMBODIMENTS

Figure 1:
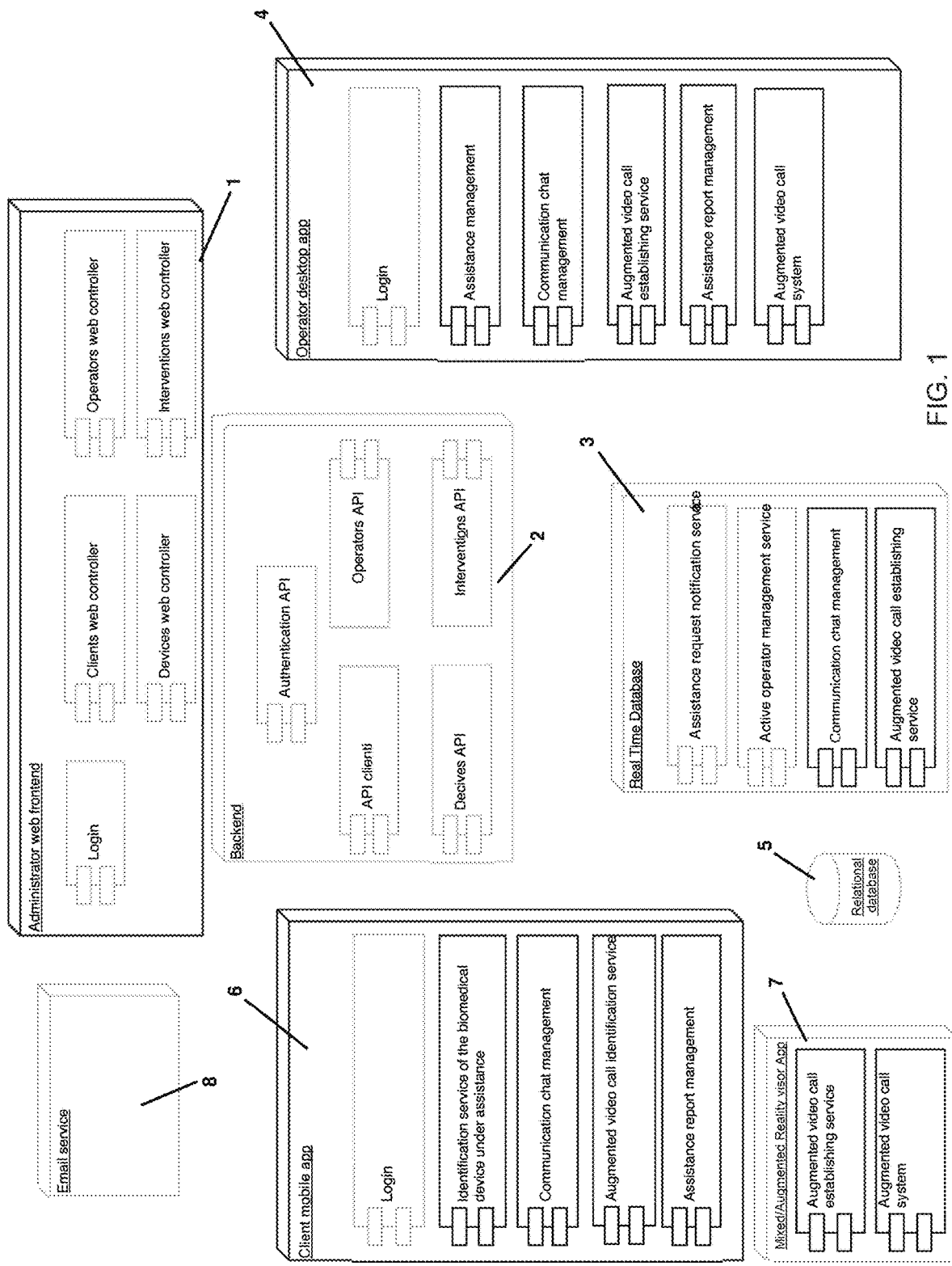
FIG. 1 is a diagram of the main elements included in the system according to the present invention.

The architecture of the system of the present invention comprises the following apparatuses:
one or more smartphones/tablets of each user who requests assistance, which can be connected to any mixed/augmented reality visor on which a specific app (7) is installed,
one or more operator stations with PC/tablet configured to be able to communicate in real time with the devices (smartphones/tablets) of the users who request assistance,
at least one server configured to manage a database and to be connectable and interfaceable with said smartphones/tablets of the users and said PCs/tablets of the operators,
wherein said smartphones, tablets, PCs, visors and servers are configured to implement the following software components, diagrammatically shown in FIG. 1, which are all connectable to an Internet network:
1. ADMINISTRATOR WEB FRONTEND
2. BACKEND
3. REAL TIME DATABASE
4. OPERATORS DESKTOP APP
5. RELATIONAL DATABASE
6. CLIENTS MOBILE APP
7. MIXED/AUGMENTED REALITY VISOR APP
8. EMAIL SERVICE 1) ADMINISTRATOR WEB FRONTEND
a. Login
Administrator login interface
b. Clients web controller
Page for performing operations on clients: listing, reading, inserting, editing, deleting
c. Device web controller
Page for performing operations on devices: listing, reading, inserting, editing, deleting
d. Operators web controller
Page for performing operations on operators: listing, reading, inserting, editing, deleting
e. Interventions web controller
Page for performing operations on interventions: listing, reading, viewing report
2) BACKEND
a. Authentication API
Server function for authenticating users on system
b. Clients API Server function exposing operations on clients: listing, reading, inserting, editing
c. Operators API
Server function exposing operations on operators: listing, reading, inserting, editing
d. Devices API
Server function exposing operations on devices: listing, reading, inserting, editing
e. Interventions API
Server function exposing operations on interventions: listing, reading, inserting and viewing reports
3) REAL TIME DATABASE
a. Assistance request notification service
Service which intercepts an assistance request and notifies it to the available operators
b. Active operator management service
Available operator notification service
c. Communication chat management
Real time two-way chat service between assistance requester and operator
d. Augmented video call establishing service
Augmented video call communication handshaking service
4) OPERATOR DESKTOP APP
a. Login
Operator authentication interface
b. Assistance management
Interface for viewing assistance requests, seeing details and taking charge of one
c. Communication chat management
Operator chat interface
d. Augmented video call establishing service
Call handshaking request interface
e. Assistance report management
Assistance report insertion and sending interface
5) RELATIONAL DATABASE
Database containing the users accounts, the devices, the companies (clients and of assistance), the operations and the reports
6) CLIENT MOBILE APP
a. Login
User authentication interface
b. Identification service of the biomedical device under assistance
Recognition system by means of optical recognition identification of the device
c. Communication chat management
User chat interface
d. Augmented video call identification service
Call handshaking interface
e. Assistance report management
Assistance report viewing 7) MIXED/AUGMENTED REALITY VISOR APP
Application which activates the video assistance handshaking by pairing the devices by means of number code, wherein said handshaking substantially allows to exchange messages on network, preferably in HTML format.
8) EMAIL SERVICE
Email service for:
Notifying the activation of the accounts of operators and clients
Sending the final assistance report Operation Scenarios In the operation scenario, it is important to note that, as mentioned, all the devices and software components mentioned above with reference to the system architecture must have access to an Internet network.

Figure 12:
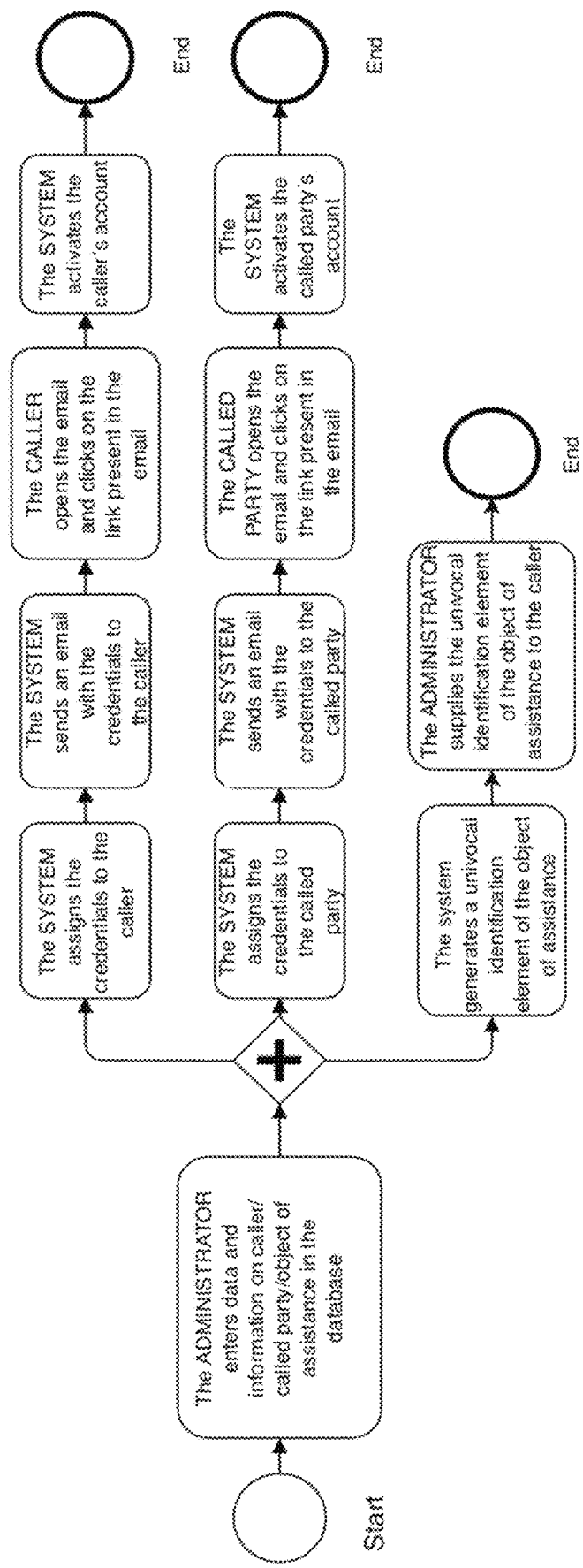
Figure 13:
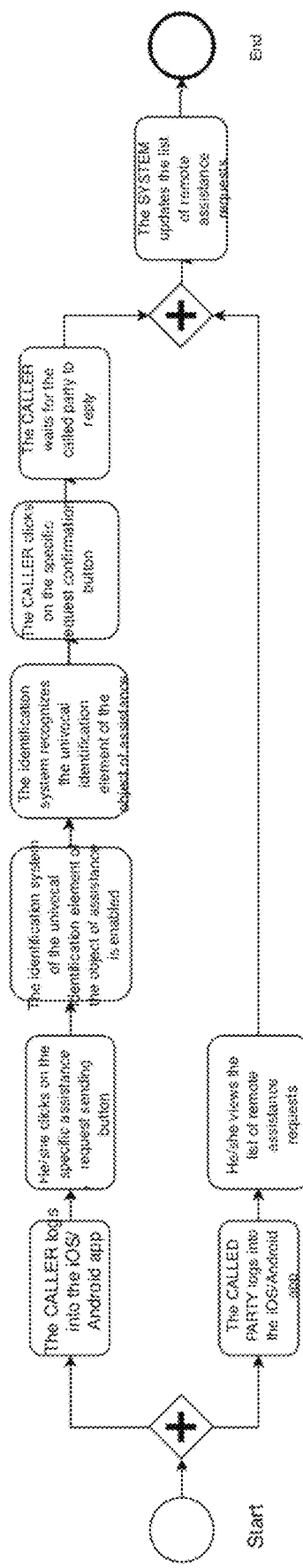
Figure 14:
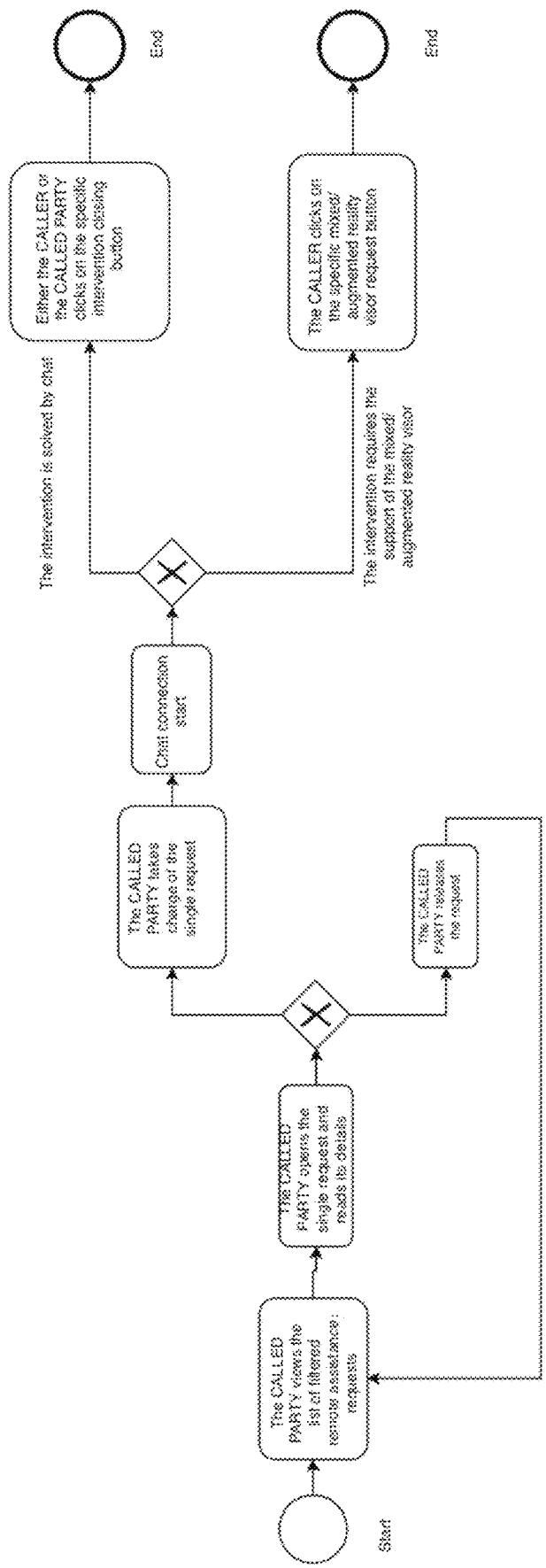
Figure 15:
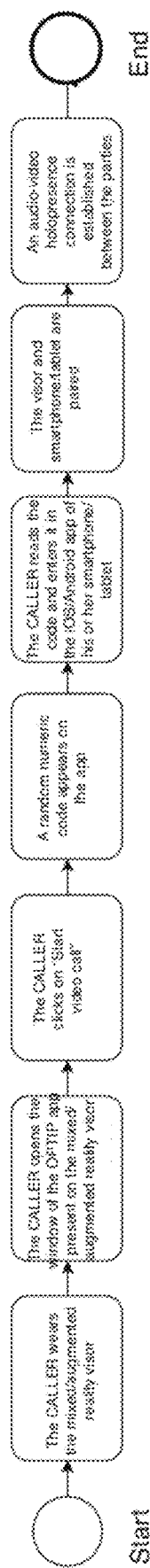
Figure 16:
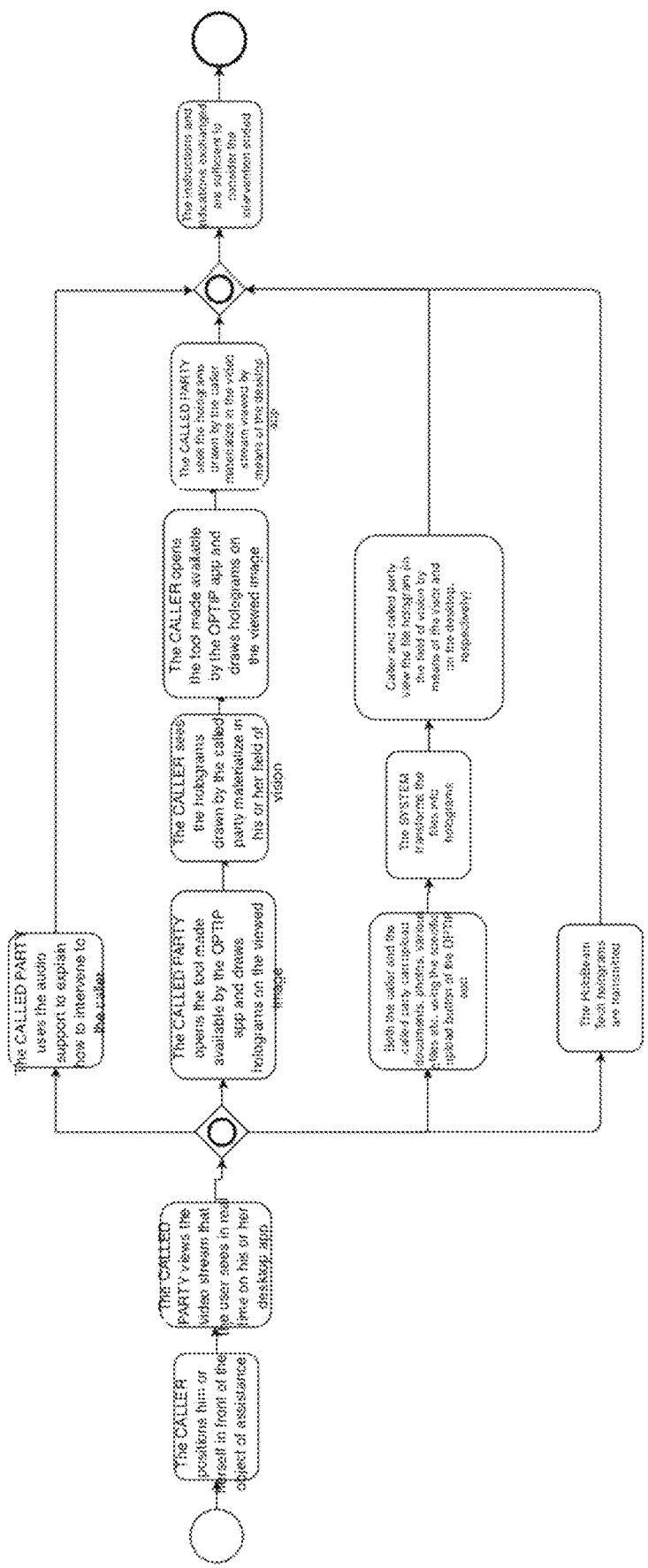

With reference to FIG. 12, the System Administrator, by means of his or her web application (1), catalogs the data related to each single CALLER (i.e. the user who requests assistance) and the CALLED PARTY (i.e. the operator who provides assistance) in the database (5): the access credential to the respective software applications on smartphone/tablet and on PC/tablet are thus assigned to each one.

The respective access credentials, together with an account activation link, are then sent by email in automated manner to each caller and called party.

The System Administrator also catalogs the assistance objects with respective information which are enclosed in a univocal identification element generated by the system itself, such as, for example, QR code, a barcode or alphanumeric code or other identification suited for the purpose.

The remote assistance system is ready to be used once the users and operators enabled to access have been registered and cataloged as "callers" and "called parties", respectively.

From the operative point of view, the process starts with the request for remote presence service by a caller by means of the mobile application (6) as shown below:

The caller logs on with the credentials provided to him or her by the Administrator and requests the call by means of the specific button of the app.

Figure 2A:
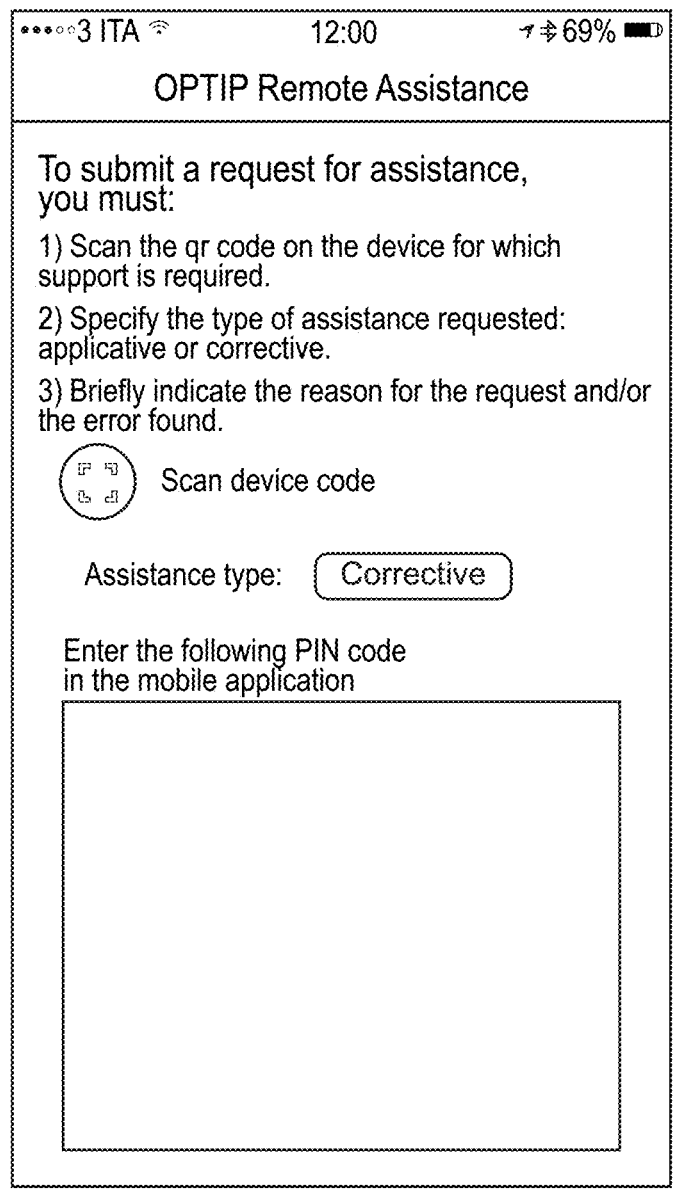
FIGS. 2A, 2B show some screenshots of the mobile app which can be installed on the caller's smartphone/tablet.
Figure 2B:
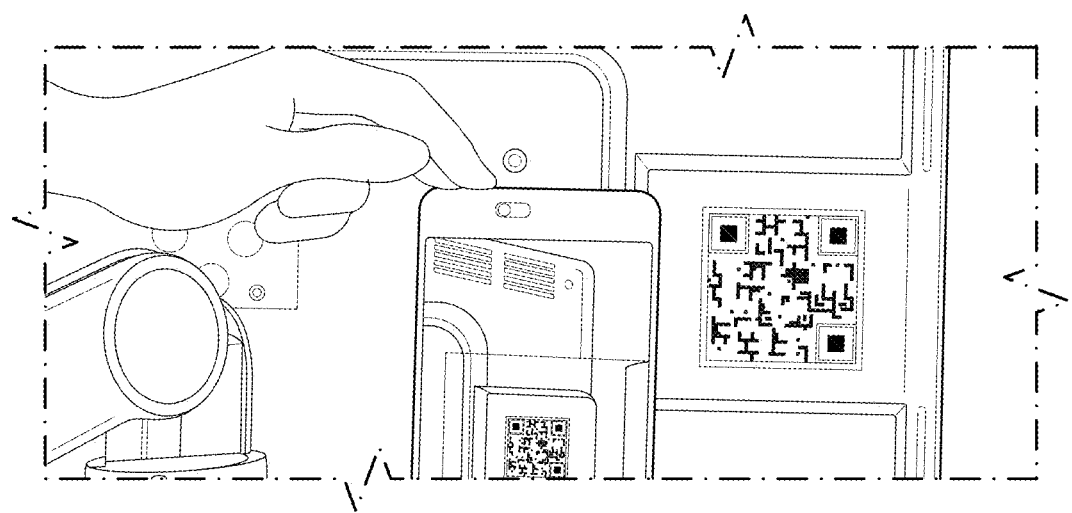

By clicking on the specific button (e.g. "Scan device code"), the application asks the caller to recognize the identification element of the object of the assistance, for example, QR code, and scan it using the camera of the device (FIG. 2B). Thereby, the request sent by the client is recorded on the backend web system (2) and processed to be assigned to a remote operator according to the requirements indicated by the caller in the "Assistance type" section (FIG. 2A) and the information contained in the identification element (QR code).

The backend software component (2) for managing requests thus assigns the request to the remote operator.

When the assigned operator views the list of intervention requests on his or her desktop application (4), preferably for Windows/iOS, and can open the request to check the description inserted by the caller (FIG. 3).

In this regard, it is worth noting that, according to the invention, an algorithm capable of storing automatic filters and directly assigning the request to a specific operator may be included (examples of assignment rules are: appropriateness, equity, role, retrievability, etc.)

In this situation, the operator can:
Take charge of the intervention request if the description is suited to his or her role and skills
Not take charge of the intervention and release it in order to allow another operator to take charge of it instead.

The operator who accepts the request starts a chat session with the user.

Two cases may occur:
1) The description provided by means of chat by the caller allows the called party to provide written indications for solving the problem and, once it has been solved, the chat session is ended, thereby concluding the remote assistance.
2) If the chat session is not sufficient to provide the solution of the problem and the intervention mode requires visual support for both parties, the called party asks the caller to wear the mixed/augmented reality visor by clicking on the specific "Request Hololens" button (FIG. 4).

Once the visor has been worn and switched on and the Windows/iOS application (7) of the mixed augmented reality visor has been opened, the caller clicks on the specific "Start video call" button and views a random identification code which he/she inserts on the application (6) of his or her iOS/Android device so as to establish the actual pairing between the visor and the device (smartphone/tablet) itself.

Figure 17:
FIGS. 17 and 18 show two screenshots of the OPTIP mixed/augmented reality visor app which can be installed on the visor, related to the starting of a video call for remote assistance in holopresence.
Figure 18:

At this point, the system starts the connection in holopresence (FIG. 17-18).

Therefore, the system activates an audio-video connection in holopresence, which also allows the transmission of holograms, keeping open the connection on both the caller's devices, i.e. smartphone/tablet and visor.

Figure 5:

In these conditions, the caller and the called party can see and talk to each other in holopresence (FIG. 5), with the possibility of drawing and positioning holograms in the visor wearer's field of vision to communicate and exchange information contents (documents, photographs, files, holograms etc.) more effectively and in real time.

Two practical cases will be analyzed below by way of non-limiting example: remote presence assistance for a technical intervention on an apparatus (Example #1) and remote presence assistance for a health care intervention on a patient (Example #2).

The entire intervention, if agreed and authorized by the user wearing the mixed/augmented reality visor, may be recorded as a video file (e.g. mp4) and used for analysis and extrapolation of Business Intelligence data or for teaching purposes.

EXAMPLE #1

The "players" involved in the process can be identified in the described scenario:
CALLER: The client who receives assistance
CALLED PARTY: Remote operator who assists the client
System Administrator We will define ultrasound apparatuses, which were previously identified in a database (5) with generation of an identification QR code for each apparatus, as an object of assistance for which intervention is required. Alternatively to the QR code, a normal barcode or other type of identification code suited for the purpose may be used.

In the present example, we will suppose the need for assistance by the client for a fault which occurred to an ultrasound apparatus.

The client opens the mixed/augmented reality visor application (6) previously installed on his or her smartphone and/or tablet and logs in with the credentials provided by the system.

The screenshot shown in FIG. 2A appears by clicking on the specific "Request assistance" button.

The client can select the "Assistance type" from a drop-down menu and describe the reason for the request for intervention.

By clicking on the "Scan device code" option, the application enables the camera of the smartphone and/or tablet, allowing the client to scan the QR code placed on the apparatus for which assistance is required by approaching the device as shown in FIG. 2B.

Thereby, the request sent by the client is recorded on the backend web system (2) and assigned to a remote operator according to the requirements indicated by the client in the "Assistance type" section and of the information contained in the QR code.

The operator—who previously logged into the desktop application (4) installed on his or her PC/tablet—views the list of the assistance requests recorded by the system and takes charge of the request conforming to his or her role and skills by clicking on the "Take charge" button, as shown in the image in FIG. 3.

Thereby, a chat aimed at detailing the problem is started between the two parties.

As previously mentioned, two cases may occur:
The description provided by means of chat to the client allows the operator to provide written indications for solving the fault (FIG. 4).
If the chat session is not sufficient to indicate the solution of the problem and the intervention mode requires visual support for both parties, the operator asks the client to wear the mixed/augmented reality visor by clicking on the specific "Request Hololens" button.

The client-after having worn the visor-opens the mixed/augmented reality visor app (7) installed on the visor itself and by clicking on the "Start video call" button will view a random numeric identification code which he/she will insert on the application (6) of his or her iOS/Android device so as to establish the pairing between the visor and the device (smartphone/tablet) itself.

A video call in holopresence is activated in this way by keeping open the connection on both of the user's aforesaid devices, i.e. on the smartphone/tablet and the visor associated therewith.

According to another particular feature of the invention, the audio-video connection in holopresence which is established by means of the app (7) installed on the visor advantageously allows to also transmit holograms.

In particular, the client wearing the visors positions him or herself in front of the part of apparatus on which it is necessary to intervene, thereby allowing the operator to view on his or her desktop app (4) the video stream of what is in front of the client in that moment.

By means of the desktop app (4) the operator uses the tools made available to draw and position holograms in the client's field of vision, in order to communicate and exchange informative contents (documents, photographs, files, holograms etc.) more effectively.

The client will see the holograms drawn by the operator materialize in real time in his or her field of vision and in turn can draw or position holograms and documents (FIG. 5) which can be also viewed by the operator.

Thereby, the client can proceed with the guided solution of the fault by means of the viewed images.

Figure 6:
Figure 7:
Figure 8:

An example of intervention with change of an ultrasound apparatus filter is described (FIG. 6, 7, 8).

The remote presence process ends with the closing of the call by the client by means of a specific button of the visor and of the smartphone/tablet.

At the end of the operation, the operator can compile a closing technical report of the intervention required by the system, which is recorded in the database (5) and sent to the customer by email.

All information on the entire intervention is kept in the database (5) itself.

It is worth noting that the process described hereto may be used for any type of request.

EXAMPLE #2

The players involved in the process can be identified in the described scenario:
Patient for whom medical assistance is required
CALLER: Caregiver (nurse, relation of the patient, etc.)
CALLED PARTY: Remote doctor who assists the Caregiver
System Administrator We will define the patient, whose personal information and medical files were preliminary identified in the database (5) with generation of identification QR code or other code suited to the purpose, as object of assistance for which intervention is required.

In the present example, the need for assistance which consists in a medical visit for heart failure is supposed.

Similarly to that described in Example #1, the Caregiver opens the mixed/augmented reality visor application (6) previously installed on his or her smartphone and/or tablet and with the credentials provided by the system, logs in and clicks on the specific "Request assistance" button.

The Caregiver describes the reason for the request in the specific space.

By clicking on the "Scan device code" option, the application enables the camera of the smartphone and/or tablet, allowing the client to scan the QR code previously assigned to the patient by approaching the device thereto.

Thereby, the request sent by the Caregiver is recorded on the backend web system (2) and assigned to a remote doctor according to the requirements indicated by the Caregiver and the information contained in the QR code.

The doctor—who previously logged into the desktop application (4) installed on his or her PC/tablet—views the list of assistance requests recorded by the system and takes charge of the request by clicking on the "Take charge" button, as shown in the image in FIG. 9.

Thereby, a chat aimed at detailing the problem is started between the two parties.

Two cases may occur:
1) The description provided by means of chat by the Caregiver allows the doctor to provide written indications to intervene on the patient and end the remote assistance session.
2) If the chat session is not sufficient to indicate the solution of the problem and the intervention mode requires visual support for both parties, the doctor asks the Caregiver to wear the mixed/augmented reality visor by clicking on the specific "Request Hololens" button.

The Caregiver-after having worn the visor-opens the mixed/augmented reality visor app (7) present on the visor itself and by clicking on the "Start video call" button will view a random numeric identification code which he/she will insert on the application (6) of the iOS/Android device so as to establish the pairing between the visor and the device (smartphone/tablet) itself.

A video call in holopresence is thus activated keeping open the connection on both the devices.

The audio-video connection in holopresence also allows the transmission of holograms.

In particular, the Caregiver wearing the visor positions him or herself in front of the patient, thereby allowing the doctor to view on his or her desktop app (4) the video stream of what is in front of the Caregiver in that moment.

By means of the desktop app (4), the doctor uses the elements/tools made available to draw and position holograms in the Caregiver's field of vision, in order to communicate and exchange informative contents (documents, photographs, files, holograms etc.) more effectively.

Caregiver sees the holograms drawn by the doctor materialize in real time in his or her field of vision and can draw and position holograms and documents in turn using the app (7) present in the visor.

Figure 10:
FIGS. 10 and 11, similar to FIGS. 5-8, relate to an assistance intervention in the case of a patient;
FIGS. from 12 to 16 show a diagram of the method, divided into 5 sequential parts corresponding to an equal number of diagrams from A to E.
Figure 11:

Thereby, the CAREGIVER, by means of the viewed images and the received indications may interact correctly with the patient (FIGS. 10-11).

The process ends with the closing of the call, which may be performed by the caller by means of a specific button, both on the app (7) of the visor and on the app (6) of his or her smartphone/tablet, or by the called party by means of a specific button of the app (4) of his or her PC/tablet.

At the end of the intervention, the doctor by clicking on the "Compile summary document" will compile a document which is recorded in the database (5) and sent to the patient by email.

All information on the entire intervention is kept in the database (5) itself.

It is worth noting that the described process may be used for any type of request.

A process diagram divided into 5 sequential parts shown in FIGS. from 12 to 16 is provided below.

With reference to figures from 12 to 16, the method according to the present invention includes the following steps:

a) The caller, who requires assistance, starts the application (6) on his or her smartphone/tablet and requests assistance with his or her credentials, enabling the recognition means of the univocal identification element of the object of assistance.
b) The backend application (2) receives the assistance request from the caller and sends it to the desktop application (4) of all the operators active at that time.
c) At least one of the active operators examines the assistance request and decides whether to take charge of the request or to release it to those of which to be taken charge.
d) If an operator in the preceding step decides to take charge of the request, the operator starts a chat with the caller.
e) The caller in the chat explains what is needed and the operator provides the required information.
f) If the exchange of information by means of chat is sufficient to provide the required assistance, the connection is closed by the operator or by the caller and the remote assistance procedure ends there, otherwise the method goes to the next step.
g) If the information exchange by means of chat is not sufficient to provide the required assistance, the operator asks the caller to wear the mixed/augmented reality visor.
h) The caller wears the visor and starts the OPTIP mixed/augmented reality visor (7) application installed thereon to start a video call.
i) An mixed/augmented reality visor app shows a random numeric code on the visor.
j) The caller enters such a code on his or her smartphone/tablet.
k) A pairing is established between visor and smartphone/tablet and an audio/video connection in holopresence is started between caller and operator.
l) The caller positions him or herself in front of the object of the assistance and looks at it.
m) The operator views the same video stream that caller has in front of his or her eyes in real time on his or her desktop app (4) and can give instructions to the caller by means of the audio-video support.
n) The operator using the tools made available on the desktop app (4) draws holograms on the viewed image and/or adds multimedia contents that the caller sees in real time on his or her field of vision.
o) The caller using the tools made available to him or her on the mixed/augmented reality visor app (7) in turn draws holograms on the viewed image and/or adds multimedia contents that the operator sees in the real time in the video stream viewed by means of the desktop app (4).

p) Once the exchange of audio/video information has ended and the remote assistance has been concluded, the connection is interrupted by the operator or by the caller and the remote assistance procedure ends here.

With reference to FIG. 12, according to the invention, a preliminary step of recording is included in which the System Administrator enters into the database the data related to each caller, each called party and each object of the assistance enabled to interface with the system itself in order to create a user-operator-apparatus (or patient) master file and to generate a univocal identification for each apparatus/patient. Such a univocal identification is preferably a QR code and may be a barcode or alphanumeric code or a serial number or any other univocal identification suited for the purpose.

In particular, the gateways used in FIGS. 12-16 have the following meanings:

| Gateway | | Description |
|---|---|---|
| ⊕ | Parallel | This indicates that the activities which follow must be all performed in parallel. |
| ⊗ | Exclusive | This indicates that the activities which follow must be performed in exclusive manner, i.e. one 1 of the branches will occur |
| ◇ | Inclusive | This indicates that the activities which follow must be performed in inclusive manner, i.e. 1 of the branches will occur or all. |

The invention claimed is:

1. A method for providing remote assistance services using mixed and/or augmented reality visors by a system including:
   one or more smartphones/tablets of one or more users who request assistance, connectable to any of the mixed and/or augmented reality visors on which a specific application is installed,
   one or more operator stations each with a PC/tablet configured to communicate in real time with the one or more smartphones/tablets of the one or more users requesting assistance, and
   at least one server configured to manage a server database and to be connectable to and interfaceable with said one or more smartphones/tablets of the one or more users and said PC/tablet of the one or more operator stations,
   wherein said one or more smartphones/tablets, the one or more operator stations, and the at least one server are connected to one another and to the Internet and include one or more processors configured to implement:
      an assistance request notification service that intercepts an assistance request and notifies the intercepted assistance request to available operators of a plurality of operators,
      an active operators management service that notifies the available operators,
      a communication chat management that provides real time two-way chat service between a user that is a caller who requests assistance using the one or more smartphones/tablets and one of the available operators, and
      an augmented video call communication handshaking service,
   wherein a relational database stores accounts of the one or more users, the plurality of operators, the one or more smartphones/tablets, companies of clients and assistance, interventions and reports, and univocal identification elements of apparatuses or people requiring assistance, and
   wherein one or more of the one or more smartphones/tablets, the one or more operator stations, and the at least one server is configured to store automatic filters and directly assign the assistance request to a specific operator, based on assignment rules, the method comprising:
   receiving an input by the caller who requires assistance to start a client mobile application on one of the smartphones/tablets of the caller and request assistance with access credentials of the caller, enabling recognition of a univocal identification element of an object of assistance;
   receiving, by a backend application, an assistance request from the caller and sending the assistance request to an operator desktop application of all the operators active at a time the assistance request is received;
   providing an algorithm configured to store automatic filters and directly assign the assistance request to a specific one of the operators, based on assignment rules;
   examining, by at least one of the active operators, assistance request and determining whether to take charge of the assistance request or to release the assistance request to other operators to take charge of the assistance request;
   when at least one of the active operators takes charge of the assistance request, the at least one active operator starts a chat with the caller via a connection;
   receiving in the chat an explanation from the caller as to requested information and providing, by the at least one active operator, required information;
   when the provided required information that is provided by the chat is sufficient to provide the required assistance, closing the connection by the at least one active operator or by the caller; and
   when the provided required information provided by the chat is not sufficient to provide the required assistance, asking, by the at least one active operator, the caller to wear one of the mixed/augmented reality visors,
      when a mixed/augmented reality visor application installed on the mixed/augmented reality visor is started by the caller to start a video call, showing a random numeric code on the visor,
      when the random numeric code is entered by the caller on the smartphone/tablet of the caller, establishing a pairing between the mixed/augmented reality visor and the smartphone/tablet and starting an audio, video, or audio and video connection in holopresence between the caller and the at least one active operator,
      when the caller positions themselves in front of the object of the assistance and looks at the object of assistance,
   viewing, by the at least one active operator, a video stream on the operator desktop application of a viewed image, the video stream corresponding to a real-time view that the caller has in and providing instructions to the caller by the audio, video, or audio and video connection,
   providing, by the at least one active operator using tools of the operator desktop application, one or more of operator-provided holograms on the viewed image and operator-provided multimedia contents that the caller sees in real time in a field of vision of the caller, viewing by the at least one active operator on the operator desktop application, one or more of caller-provided holograms drawn by the caller on the viewed image and caller-provided multimedia contents that the at least one active operator is able to see in the real time in the video stream, and after an exchange of audio-video information ends and the remote assistance services conclude, interrupting the connection by the at least one active operator or the caller.

2. The method according to claim 1, further comprising:

cataloging in the relational database, by a system administrator by an administrator web application, data related to each caller that is the user who requests assistance, and each called party that is the at least one active operator who provides assistance, to assign the access credentials to the respective operator desktop application and the client mobile application on the smartphone/tablet and on the PC/tablet, sending the respective access credentials, together with an account activation link, by email in an automated manner to each caller and called party, and cataloging, by the system administrator, assistance objects with respective information which are enclosed in a univocal identification element generated by the system such that the system is ready to be used after the users and the operators that are enabled to access as callers and called parties, respectively, are registered and cataloged.

3. The method of claim 1, wherein the univocal identification element is a QR code.

* * * * *